United States Patent [19]

Müller-Späth

[11] Patent Number: 5,792,102
[45] Date of Patent: Aug. 11, 1998

[54] CONVERSION KIT FOR A MACHINE FOR AUTOMATIC INTRAVASCULAR INJECTION OF SOLUTIONS

[75] Inventor: Reinhard Müller-Späth, Much, Germany

[73] Assignee: Mallinckrodt Medical, Inc., St. Louis, Mo.

[21] Appl. No.: 687,464

[22] PCT Filed: Jan. 25, 1995

[86] PCT No.: PCT/US95/01152

§ 371 Date: Nov. 19, 1996

§ 102(e) Date: Nov. 19, 1996

[87] PCT Pub. No.: WO95/20410

PCT Pub. Date: Aug. 3, 1995

[30] Foreign Application Priority Data

Jan. 28, 1994 [EP] European Pat. Off. ............... 9401290

[51] Int. Cl.$^6$ ............................................. A61M 5/20
[52] U.S. Cl. ............................................. 604/70; 604/154
[58] Field of Search ........................... 604/141, 143, 604/144, 152, 154, 155, 70, 71, 39, 97, 98, 283

[56] References Cited

U.S. PATENT DOCUMENTS

| | | |
|---|---|---|
| 3,858,581 | 1/1975 | Kamen . |
| 4,596,558 | 6/1986 | Smith et al. . |
| 4,677,980 | 7/1987 | Reilly et al. . |
| 4,705,509 | 11/1987 | Stade . |
| 5,080,653 | 1/1992 | Voss et al. . |
| 5,140,862 | 8/1992 | Pappalardo . |
| 5,244,461 | 9/1993 | Derlien . |
| 5,269,762 | 12/1993 | Armbruster . |

*Primary Examiner*—Michael Buiz
*Assistant Examiner*—William W. Lewis
*Attorney, Agent, or Firm*—Lawrence L. Limpus

[57] ABSTRACT

The present invention relates to a conversion kit for converting a machine designed for intravascular injection of solutions, such as parenteral solutions, using high-pressure syringes, to a machine that can be used for injection using smaller manual syringes. The conversion kit, includes at least one conversion vessel (13) for releasable but substantially non-rotary reception of a high-pressure syringe with a cylindrical guide (19) formed through a receiving head (14) of the conversion vessel (13) and a recess (17) formed in the upper surface of the receiving head (14). The recess (17) may also receive the radial end regions of wing extensions of a manual syringe of predetermined size. The conversion kit also includes at least one reducing sleeve (23) for reducing the effective inner diameter of the guide (19), the reducing sleeve (23) adapted to snugly receive the outer diameter of a manual syringe (12). The reducing sleeve also includes a peripheral edge (26) which is adapted to be received in the recess (17). The conversion kit also includes at least one conversion piston holder (29), with a maximum diameter equal to or less than the diameter of the piston (11) of the manual syringe (12), the conversion piston holder (29) being equipped with a mechanism (30) for releasably securing it to the free end of a spindle (10) of the machine and with a coupling head (31) for coupling the conversion piston holder (29) to the piston of a high-pressure syringe or for applying injection pressure to the piston (11) of the manual syringe (12).

11 Claims, 6 Drawing Sheets

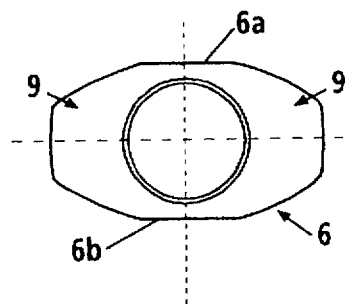
Fig. 10
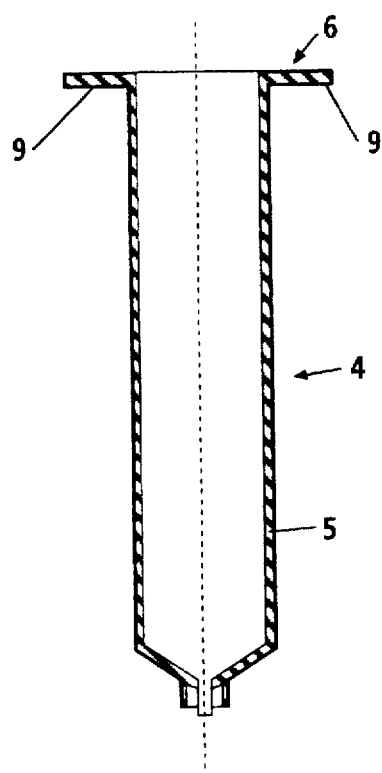

CONVERSION KIT FOR A MACHINE FOR AUTOMATIC INTRAVASCULAR INJECTION OF SOLUTIONS

BACKGROUND

The present invention relates to a conversion kit for a machine for intravascular injection of compounds or solutions, such as parenteral solutions, e.g. X-ray contrast medium solutions, from high-pressure syringes. In particular, the present invention relates to a conversion kit which enables the use of an injection machine designed for high-pressure syringes to be use with manual syringes.

In general, injection machines for high-pressure syringes include a vessel for releasably holding a high-pressure syringe and a power-driven retractable and extendable spindle for moving the piston of the high-pressure syringe. The vessel has a receiving head provided with a cylindrical guide for tightly surrounding the distal end region of the high-pressure syringe body and having a radial recess for substantially non-rotary reception of a peripheral edge projecting from the distal end of the high-pressure syringe body. The spindle has a piston-holder releasably secured to its free end, the piston-holder having a coupling head for coupling it to the piston of the high-pressure syringe.

Injection machines are used for intravascular injection of parenteral solutions, more particularly X-ray contrast medium solutions, in phlebography, i.e. X-ray photography of leg veins for diagnosing thrombosis, and in computer tomography, in order to inject relatively large volumes, in the range of about 100 to 200 ml, in accordance with a set controlling program. In this manner, a wide variety of desired injection profiles can be obtained with a high degree of accuracy, and in a simple manner, while meeting the particular medical requirements. The various injection profiles can be stored and are therefore always available for further inspection and for future investigations.

For example, injection machines can deliver parenteral solution at rates from 0.1 to 9.9 ml/s, which can be selected in 0.1 ml/s steps, and total injected volume of about 100 to 200 ml, being injectable in portions which can be selected in 1 ml steps. Injection is carried out at relatively high pressure, in the range of several bars to several tens of bars, the pressure being electronically controlled and limited for safety reasons.

Injection machines use syringes which usually have a relatively large volume of about 100 to 200 ml. These syringes are known in clinical terminology as "high-pressure syringes" because of the relatively high pressure used for injection.

In addition to high-pressure syringes for injection machines, there is a continuing and much more extensive use in medical practice of conventional manual syringes, which usually have a relatively small volume in the range from 1 to 50 ml. In many cases it would be very desirable to use manual injection syringes in automatic injection procedures. However, manual injection syringes are generally constructed in a manner which does not fit in automatic injection machines designed for high-pressure syringes. Therefore a special machine which is designed for manual injection syringes is needed. These special machines are relatively expensive, and thus add to the overall cost of performing medical procedures.

Therefore, there remains a need in the art to provide a less complex and less expensive means and procedure for performing automatic intravascular injection of parenteral solutions from manual syringes.

OBJECTS OF THE INVENTION

It is one object of the present invention to provide a conversion kit which allows an automatic injection machine for high-pressure syringes to be optionally used for automatic injection using manual syringes.

SUMMARY OF THE INVENTION

The above object and others as will be apparent to one skilled in the art are accomplished according to the present invention by providing a conversion kit for enabling automatic injection machines designed for high-pressure syringes to be used for intravascular injection from manual syringes. In particular, the conversion kit according to the present invention includes the following elements.

(1) At least one conversion vessel, having a receiving head with a radial recess including a first region for substantially non-rotary reception of the peripheral edge projecting from the distal end of a high-pressure syringe, and also including a second region for receiving the radial end regions of the wings of a manual injection syringe of predetermined size. The conversion vessel replaces the original vessel of the injection machine.

(2) At least one reducing sleeve for reducing the effective inner diameter of the cylindrical guide of the injector machine. The reducing sleeve includes a substantially cylindrical sleeve member, having an outer diameter which will fit snugly within the inner diameter of the cylindrical guide and having an inner diameter which will snugly receive the outer diameter of the manual syringe. The reducing sleeve also includes a peripheral edge projecting radially from the distal end of the reducing sleeve and adapted to be received in the first region of the radial recess in the receiving head, and in which the peripheral edge of the distal end of the manual syringe can be received.

(3) At least one conversion piston holder, having a radial maximum diameter equal to or less than the diameter of the piston of the manual syringe. The conversion piston holder is equipped with a means for releasably securing the conversion piston holder to the free end of the spindle of the injection machine and also is equipped with a head for coupling the piston holder to the piston of a high-pressure syringe and for applying pressure to the piston of the manual syringe. The conversion piston holder replaces the original piston holder of the injection machine.

The conversion kit according to the present invention has the advantages of providing means to quickly, easily and inexpensively convert an injection machine designed for high-pressure syringes into an injection machine for manual syringes. Another advantage of the present invention is that the conversion is not permanent and the injection machine can easily be used for either high-pressure syringes of manual syringes.

In one preferred embodiment of the present invention, the conversion kit is designed for use with 30 ml to 50 ml manual injection syringes having similar diameters but which can differ in length and for 50 ml to 200 ml high-pressure syringes.

In another preferred embodiment, the conversion kit according to the present invention includes a number of conversion vessels, a number of reducing sleeves and a number of piston-holders, so that the injection machine can be used for manual syringes having bodies which vary in diameter, e.g. for all or some selected sizes of manual syringes having diameters ranging from 1 ml to 50 ml.

In order to fit the reducing sleeve in the cylindrical guide of the head of the conversion vessel in a manner which prevents shifting by small forces exerted during handling, the conversion kit according to the present invention includes means for providing a resilient projection on the inner periphery of the cylindrical guide of the injection machine corresponding to a recess formed on the outer periphery of the reducing sleeve, or vice versa. In a particularly simple and convenient construction according to the present invention, the resilient projection is formed by an O-ring inserted into a groove formed on the inner periphery of the guide or on the outer periphery of the reducing sleeve.

The reducing sleeve of the conversion kit according to the present invention is preferably made of plastic, and particularly a resilient plastic such as polytetrafluoroethylene, polyester or polyamide.

The present invention provides several advantages, some of which have been mentioned above and others which will be described in detail with reference to a the drawing figures below.

BRIEF DESCRIPTION OF THE DRAWINGS

FIG. 10 is a cross-section view of a manual syringe without the piston, and a distal end view thereof, showing the shape of a distal radial peripheral edge including two radially opposite wings.

DETAILED DESCRIPTION OF THE INVENTION

Initially, the main differences between conventional manual syringes and high-pressure syringes, especially as such are important for understanding the present invention will be discussed with reference to FIGS. 9 and 10.

Figure 9:
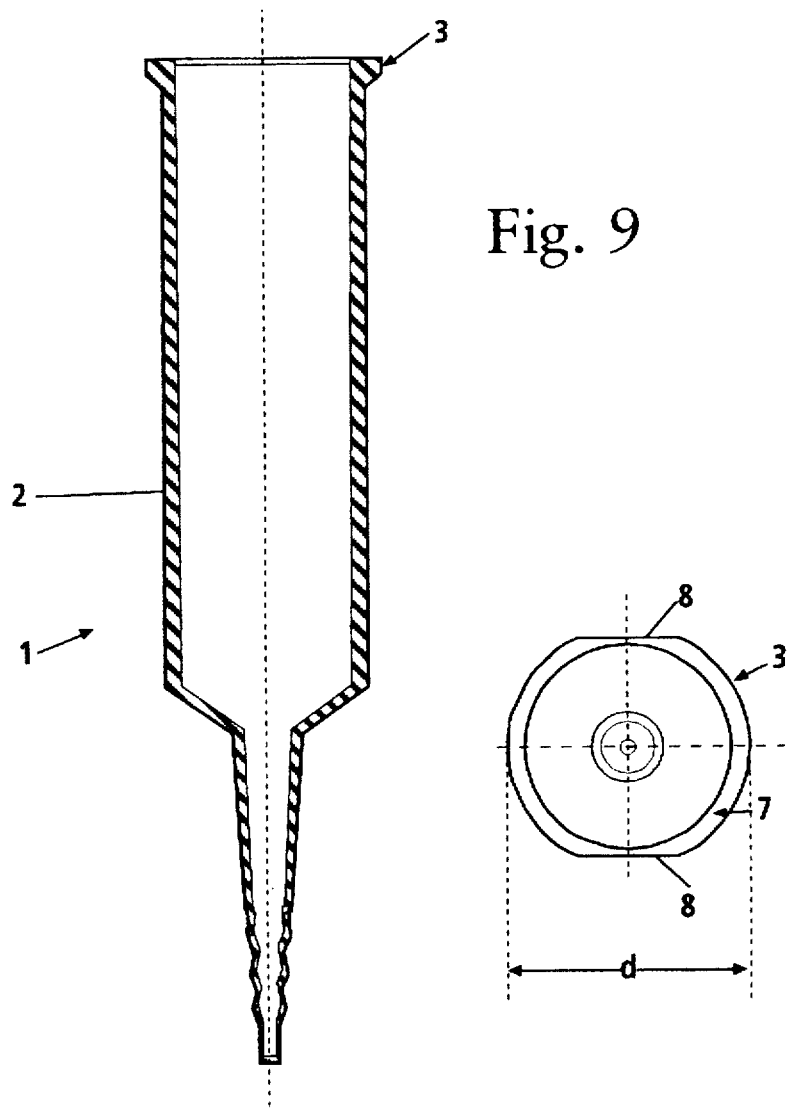
FIG. 9 is a cross-section view of a high-pressure syringe without the piston, along with a distal end view thereof, showing the shape of a peripheral edge radially projecting from the high-pressure syringe body.

FIG. 9 is a cross-section view of a conventional high-pressure syringe without the piston, along with a distal end view thereof. In particular, FIG. 9 shows a high-pressure syringe body, generally designated by reference numeral 1, having a cylinder 2, and a radially outward projecting peripheral edge 3, in the form of a cylinder handle plate at the distal end of the cylinder 2.

FIG. 10 is a cross-section view of a manual syringe without the piston, and a distal end view thereof. In particular, FIG. 10 shows a manual syringe body, generally designated by reference is numeral 4, having a cylinder 5, and a radially outward projecting peripheral edge 6, in the form of a cylinder handle plate at the distal end of the cylinder 5.

As will be readily apparent from FIGS. 9 and 10, one difference between the high-pressure syringe body 1, and the manual syringe body 4, is that the cylinder 5, of the manual syringe body 4, has both a smaller inner and outer diameter as compared with the cylinder 2, of the high-pressure syringe body 1. This is primarily because the manual syringe is designed for smaller volumes than the high-pressure syringe. Consequently, the outer diameter of the piston (not shown) of the manual syringe is also smaller than the outer diameter the piston (not shown) of the high-pressure syringe.

A further difference between high-pressure syringes and manual syringes is that the peripheral edge 6, of the manual syringe body 4, has a different shape than that of the peripheral edge 3, of the high-pressure syringe body 1. As shown in FIG. 9, the peripheral edge 3, of the high-pressure syringe body 1, comprises a ring 7, which has diametrically opposite flat edges 8. The flat edges 8, interact with the recess in the vessel of an injection machine to hold the high-pressure syringe in a substantially non-rotatable position when inserted into the injection machine, as will be more fully described below. It is noted that some high-pressure syringes have only one flat edge 8. Also as shown in FIG. 9, the peripheral edge 3, of the high-pressure syringe body 1, has a relatively short radial length, i.e. the ring 7, is relatively narrow.

In contrast, as shown in FIG. 10, the peripheral edge 6, of the manual syringe body 4, has diametrically opposite radial projections or wings 9, having a relatively great axial length, i.e. the wings 9 are relatively wide. The wings 9, of the manual syringe body 4, are generally considerably greater in width than the width of the ring 7, of the high-pressure syringe body 1, to facilitate easy manual handling of the manual syringe. Preferably, flat portions 6a, 6b, are provided along a section of the peripheral edge 6, situated between the wings 9, of the manual syringe body 4.

Figure 1:
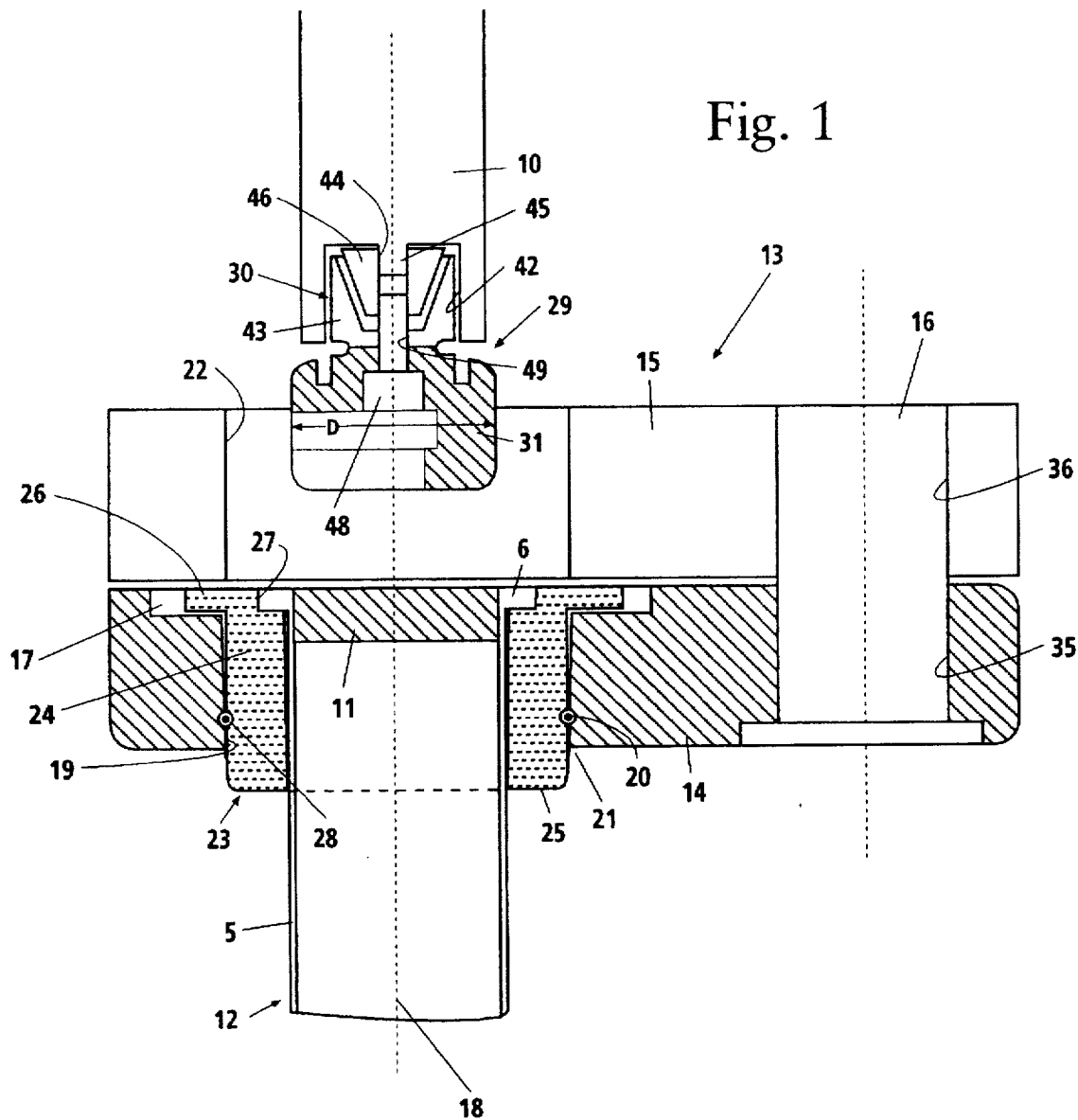
FIG. 1 is a partial diagrammatic view, mainly in cross-section, of an injection machine designed for high-pressure syringes, and including portions of the conversion kit according to the present invention.

With the above differences in mind, the conversion kit according to the present invention will now be described with reference to FIGS. 1–8. FIG. 1 is a partial diagrammatic view, mainly in cross-section, of an injection machine designed for high-pressure syringes, and including portions of the conversion kit according to the present invention. For simplicity, FIG. 1 shows only the power-driven retractable and extendable spindle 10, of the injection machine which is used to move the piston of either a high-pressure syringe or a manual syringe using the conversion kit of the present invention. In FIG. 1, the distal end region a manual syringe, generally designated by reference numeral 12, having a piston 11, is shown.

The conversion kit according to the present invention comprises a conversion vessel, generally designated by reference numeral 13, a reducing sleeve, generally designated by reference numeral 23, and a conversion piston holder, generally designated by reference numeral 29, which may be constructed and incorporated into the injection machine as follows.

The conversion vessel 13, has a plate-shaped head 14, and a plate-shaped closure member 15, which, in the present embodiment, are connected by a pivot 16, provided in bores 35, 36, so that the head 14, and closure member 15, are rotatably pivotable relative to on member 15. Upon pivoting of the closure member 15, away from the head 14, a recess 17, formed in the upper surface of the head 14, is completely exposed. Any other suitable movable connection between the head 14, and the closure member 15, may be used instead of the pivot 16, for example, a hinged or bayonet connection, or the like, provided the connection enables the closure member 15, to be moved in a manner to completely reveal the recess 17. The head 14, has a cylindrical guide 19, relative to the axis 18, which tightly surrounds the distal end region of a high-pressure syringe (not shown in FIG. 1) when the machine is using a high-pressure injection syringe. In particular, the guide 19, has a diameter which will snugly receive the outer diameter of a high-pressure syringe. The guide 19, also includes a peripheral groove 20, into which an O-ring may be inserted to form a resilient projection 21, extending into the interior of the guide 19. The closure member 15, of the conversion vessel 13, has a bore 22, which is equal in diameter to the diameter of the guide 19. The conversion vessel 13, is releasably attached to the injection machine so that either a manual or high-pressure syringe clamped in the conversion vessel 13, can be actuated by the spindle 10.

The reducing sleeve 23, is inserted into the cylindrical guide 19, thereby reducing its effective inner diameter. The reducing sleeve 23, includes a substantially cylindrical sleeve member 24, which as shown may have rounded edges at its proximal end 25, to facilitate easy insertion into the cylindrical guide 19. The outer diameter of the sleeve member 24, is dimensioned to fit snugly within the inner diameter of the guide 19, and the inner diameter of the sleeve member 24, is dimensioned to snugly receive the outer diameter of the cylinder 5, of a manual syringe 12, having a predetermined volume. A peripheral edge 26, projects radially outward from the distal end of the reducing sleeve 23, and may be received in the recess 17, in the head 14. The peripheral edge 26, which will be explained in greater detail below with reference to FIGS. 4 and 5, includes a recess 27, which is shaped so that it can receive a radial peripheral edge 6, of the manual syringe 12. In particular, a portion of the peripheral edge 6, of the manual syringe 12, is disposed radially inside the region of the peripheral edge 26, of the reducing sleeve 23, with the end regions of the wings of the manual syringe 12, projecting radially beyond the peripheral edge 26. The wings of the manual syringe 12, extend through radial recesses in the peripheral edge 26, of the reducing sleeve 23, and the end regions of the wings are received in regions of the recess 17, adapted for that purpose as will be more fully described with reference FIG. 3 below. In other words, the peripheral edge 26, of the reducing sleeve 23, and the end portions of the wings of the peripheral edge 6, of the manual syringe 12, are both received in the recess 17, of the head 14, and portions of the peripheral edge 6, of the manual syringe 12, are received in the recess 27, of the reducing sleeve 23. An indentation 28, in the form of a groove having a rounded cross-section as shown in FIG. 1, extends around the outer periphery of the sleeve member 24. The indentation 28, receives the part of the resilient projection 21, projecting into the guide 19, and helps to hold the reducing sleeve 23, more firmly within the guide 19.

The conversion piston holder 29, has a means 30, for releasably securing the conversion piston holder 29, to the free end of the spindle 10. A coupling head 31, is connected to the securing means 30, and is adapted to couple the conversion piston holder 29, to the piston of a high-pressure syringe and to apply pressure to move the piston 11, of the manual syringe 12. The maximum diameter D, defined at right angles to the axis 18, of the conversion piston holder 29, is equal to or less than the outer diameter of the piston 11, of the manual syringe 12, to allow the conversion piston holder 29, to fit within the reducing sleeve 23.

As previously noted, the conversion kit according to the present invention allows the use of an injection machine with either a manual syringe or a high-pressure syringe. In particular, the recess 17, in the head 14, is constructed so that it can receive either the peripheral edge 26, of the reducing sleeve 23, or the peripheral edge of a high-pressure syringe. Further, the recess 27, of the reducing sleeve 23, is constructed so that it can receive the peripheral edge 6, of the manual syringe 12. The conversion piston holder 29, is constructed so that the coupling head 31, can be coupled to the piston of a high-pressure syringe to enable either retraction or extension via the spindle 10. The conversion piston holder 29, can also be used to apply pressure to and move the piston 11, or the manual syringe 12. Therefore, it is only necessary to install the reducing sleeve 23, including the resilient projection 21, as shown in FIG. 1, in order to convert the injection machine designed for use with high-pressure syringes, to an injection machine for use with a manual syringe. The reducing sleeve 23, and resilient projection 21, can easily be removed to return the injection machine to its original form for use with high-pressure syringes.

Figure 2:
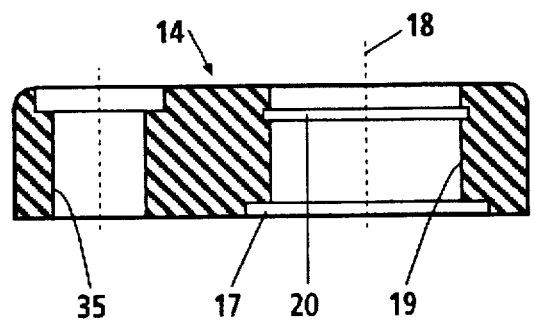
FIG. 2 is a cross-section view of the receiving head of a conversion vessel for the conversion kit according to one embodiment of the present invention.
Figure 3:
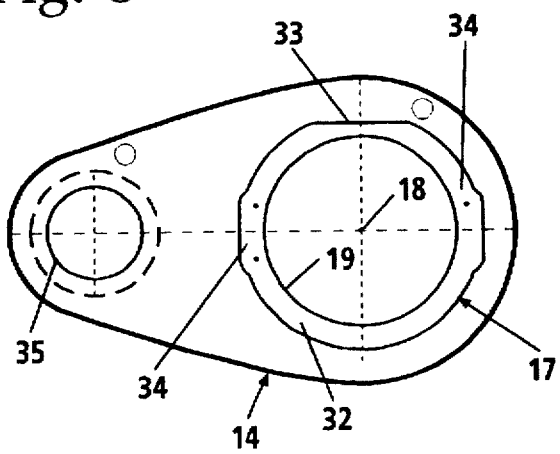
FIG. 3 is a perspective view of the bottom of the head of the conversion vessel shown in FIG. 2, i.e. showing the side from which a preferably prefilled manual syringe is inserted into the receiving head.

FIG. 2 is a cross-section view of the head 14, of the conversion vessel 13, according to one embodiment of the present invention. FIG. 3 is a perspective view of the bottom of the head 14, shown in FIG. 2, i.e. showing the side from which a preferably prefilled manual syringe may be inserted into the head 14. Together, FIGS. 2 and 3 will be used to describe details of the head 14.

The recess 17, in the head 14, includes two regions. The first region 32, is generally circular with the exception of a flat part 33. With additional reference to FIG. 9, the first region 32, acts to non-rotatably receive the peripheral edge 3, projecting from the distal end of a high-pressure syringe body 2. The flat edge 8, of the peripheral edge 3, positively engages the flat part 33, of the first recess region 32, and thus prevents the high-pressure syringe body 2, from twisting around its longitudinal axis. With additional reference to FIG. 10, the second region 34, includes two component regions for receiving the radial end regions of the wings 9, of the peripheral edge 6, provided on the manual syringe body 5.

Also shown in FIGS. 2 and 3, is the bore 35, of the head 14, the bore 35, being aligned with the corresponding bore 36, in the closure member 15, when the conversion vessel 13, is in the assembled state, and receiving a portion of the pivot 16. (Also see FIG. 1).

Figure 4:
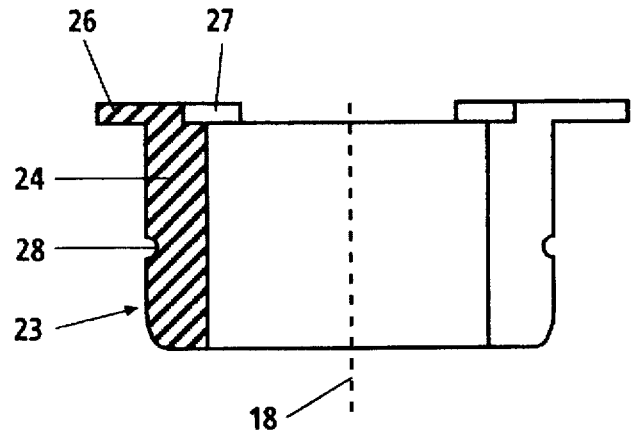
FIG. 4 is an cross-section view taken along line A—A in FIG. 5 of a reducing sleeve for a conversion kit according to the present invention.
Figure 5:
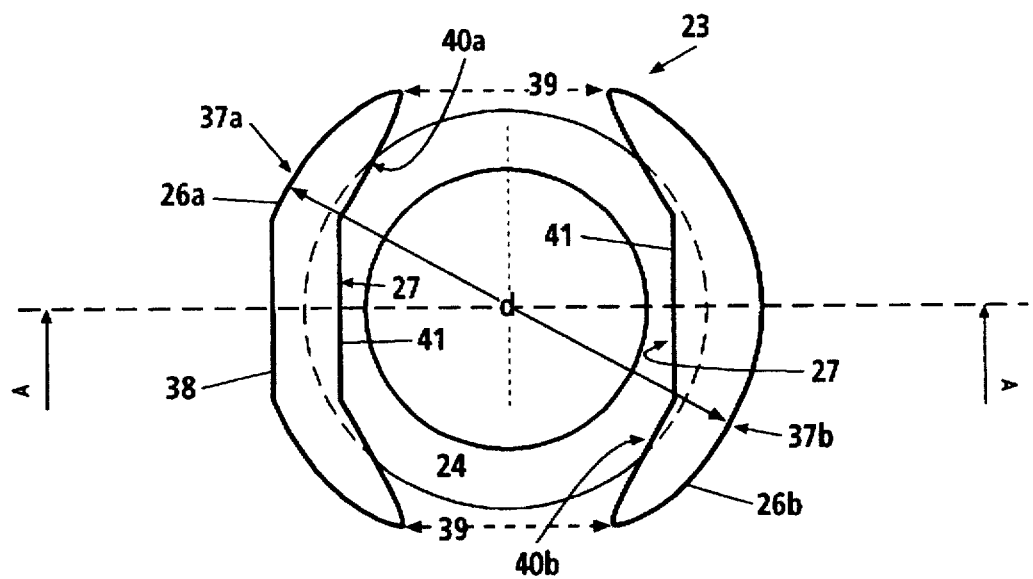
FIG. 5 is a top view of the reducing sleeve shown in FIG. 4, i.e. showing the side having the peripheral edge which is received by the recess in the head of the conversion vessel and which receives the distal peripheral edge of the manual syringe.

FIG. 4 is an cross-section view taken along line A—A in FIG. 5 of the reducing sleeve 23. FIG. 5 is a top view of the reducing sleeve 23, shown in FIG. 4, i.e. showing the side having the peripheral edge 26. Together, FIGS. 4 and 5, will be used to describe details of the reducing sleeve 23.

The peripheral edge 26, includes two parts 26a, 26b, which are diametrically opposite and extend from the periphery of the sleeve member 24. The outer configuration 37a, 37b, of the peripheral edge parts 26a, 26b, corresponds to the outer configuration of a peripheral edge of a conventional high-pressure syringe. The diameter d, of the reducing sleeve 23, in the area of the peripheral edge 26, corresponds to the outer diameter of a peripheral edge of a conventional high-pressure syringe. At least one of the two peripheral edge parts 26a, 26b, includes flat part 38. Alternatively, both peripheral edge parts 26a, 26b, can have a flat part such as shown as reference numeral 38, in FIG. 5. The edge parts 26a, 26b, extend around the periphery of the reducing sleeve 23, and are separated by a peripheral edge recess 39. The width of the recesses 39, corresponds to the width of the wings of a convention manual syringe.

The inner configuration 40a, 40b, of the peripheral edge parts 26a, 2b, corresponds to the outer configuration of a peripheral edge of a convention manual syringe. With further reference to FIG. 10, the inner configurations 40a, 40b, each include a flat part 41, corresponding to respective flat parts 6a, 6b, of the peripheral edge 6, of the manual syringe body 4. Therefore, when a manual syringe body 4, is inserted through the reducing sleeve 23, the peripheral edges 6, align and fit within the flat parts 41, and the wings 9, protrude through the recesses 39. In this manner, the manual syringe body 4, is held securely in place.

In a similar manner and with further reference to FIGS. 1, 2 and 3, the peripheral edge 26, of the reducing sleeve 23, is aligned with and is positively received by the recess 17, in the head 14. The wings 9, of the manual syringe body 4, extend through the edge recesses 39, of the reducing sleeve 23, and are received within the second regions 34, of the recess 17. Therefore, both reducing sleeve 23, and manual syringe body 4, are held firmly in place.

Figure 6:
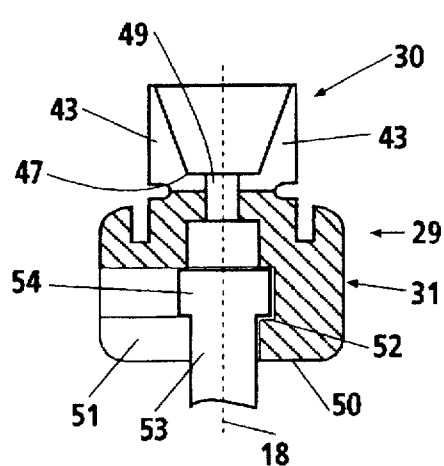
FIG. 6 is an cross-section view taken along line B—B of FIG. 7 of a portion of a conversion piston holder for a conversion kit according to the present invention.
Figure 7:
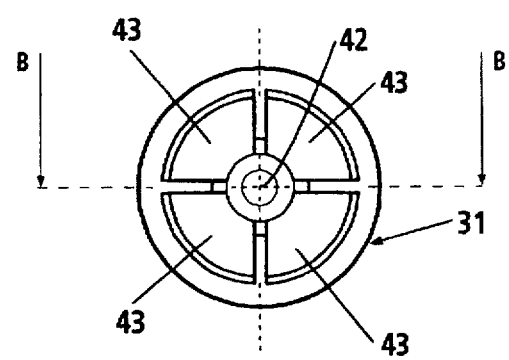
FIG. 7 is a top view of the conversion piston holder shown in FIG. 6, i.e. showing the side which faces the retractable and extendable spindle of the injection machine.
Figure 8:
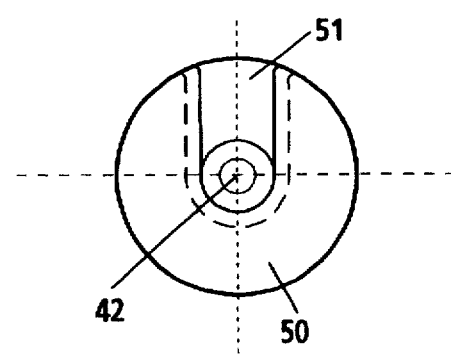
FIG. 8 is a bottom view of the conversion piston holder shown in FIG. 6, i.e. showing the side which contacts and moves the piston of the manual syringe and which can be releasably connected to the piston of a high-pressure syringe.

FIG. 6 is an cross-section view taken along line B—B of FIG. 7 of a portion of the conversion piston holder 29. FIG. 7 is a top view of the conversion piston holder 29, shown in FIG. 6, i.e. showing the side which faces the retractable and extendable spindle 10, of the injection machine. FIG. 8 is a bottom view of the conversion piston holder 29, shown in FIG. 6, i.e. showing the side which contacts and moves the piston 11, of the manual syringe 12, and which can be releasably connected to a the piston of a high-pressure syringe. Together, FIGS. 6, 7 and 8 will be used to describe details of the conversion piston holder 29.

With further reference to FIG. 1, the conversion piston holder includes securing means 30, in the form of a clamping device for radial clamping within a cylindrical bore 42, in the free end of the spindle 10. In particular, the securing means 30, includes four segments 43, of a cone shaped member disposed around the axis 18, and a bore 49, extending through the base 47, of the segments 43. A second cone member 46, is provided within the segments 43, and includes a threaded bore 44, corresponding to the bore 49. To firmly seat the second cone member 46, within the segments 43, a screw 48, can be screwed from beneath into the threaded bore 44. Further, a threaded pin 45, on the spindle 10, is screwed into the threaded bore 44, from above, and acts to press the second cone member 46, against the segments 43, and thus clamp the segments 43, firmly within the bore 49. The segments 43, base 47, and coupling head 31, may be formed integrally, of in the alternative, the base 47, may be permanently connected to the coupling head 31, by any suitable means.

The coupling head 31, has a diameter D, which is equal to or less than the diameter of the piston 11, of the manual syringe 12, and includes a flat pressure surface 50, on the end opposite from the securing means 30. The flat pressure surface 50, serves to engage the flat rear of piston 11, and is used to move the piston 11, by extension of the spindle 10, to carry out injection of the material within the manual syringe 12. The coupling head 31, also includes a slot-like radial indentation 51, which has an undercut part 52, which serves to loosely receive a pin 53, having a thick end 54, which is provided on the rear surface of the piston of a conventional high-pressure syringe. In this manner, the piston of a high-pressure syringe can be retracted by the spindle 10, to create a suction stroke for filling the high-pressure syringe or the piston of a high-pressure syringe can be pressed forward by extension of the spindle 10, to create a pressure stroke for injecting material from the high-pressure syringe.

As described in detail above, the conversion kit according to the present invention is very advantageous in providing a quick, easy and inexpensive means to convert an injection machine designed for high-pressure syringes into an injection machine for manual syringes. Also, as noted previously, because the conversion kit according to the present invention does not become a permanent part of the injection machine, the injection machine can easily be returned to its original use of injection from high-pressure syringes. Actually, all that is required for conversion from one type of syringe to the other is the placement or removal of the reducing sleeve in or from the injection machine. When the reducing sleeve is in place, the injection machine is adapted for use with manual syringes, and when the reducing sleeve is removed, the injection machine is adapted for use with high-pressure syringes. The conversion vessel and conversion piston holder as described above can be used with either manual or high-pressure syringes. However, additional sizes or conversion vessels and conversion piston holders can be provided in the conversion kit of the present invention in order to provide means for the injection machine to be used with a wide range of manual syringe sizes.

The foregoing has been a description of certain preferred embodiments of the present invention, but is not intended to limit the invention in any way. Rather, many modifications, variations and changes in details may be made within the scope of the present invention.

What is claimed is:

1. A conversion kit for a machine for intravascular injection of solutions from high-pressure syringes, the machine including a vessel for releasably holding a high-pressure syringe and a power-driven retractable and extendable spindle for moving a piston of a high-pressure syringe and provided with a piston holder for coupling with said high-pressure syringe; said conversion kit, providing means to equip said machine for use with either high-pressure syringes or for use with manual syringes of a predetermined size; said conversion kit comprising:

at least one conversion vessel for replacing said conversion vessel of said machine and for releasably holding a high-pressure syringe, said conversion vessel having a receiving head provided with a cylindrical guide for tightly surrounding the distal end region of the body of said high-pressure syringe; and a first radial recess formed in the upper surface of said receiving head, for substantially non-rotary reception of a peripheral edge projecting from the distal end of the body of said high-pressure syringe;

at least one reducing sleeve for reducing the effective inner diameter of said cylindrical guide, said reducing sleeve including:

a substantially cylindrical sleeve member having an outer diameter dimensioned to fit snugly within the inner diameter of said guide and having an inner diameter dimensioned to snugly receive the outer diameter of the body of a manual syringe;

a peripheral edge radially projecting from the distal end of said reducing sleeve, and adapted to be received said first recess in said receiving head; and a second recess formed in an upper surface of said reducing sleeve and adapted to receive a distal peripheral edge of said manual syringe; and at least one conversion piston holder for replacing said piston holder of said machine having a maximum diameter which is equal to or less than the diameter of a piston of said manual syringe, said conversion piston holder including means for releasably securing a first end of said conversion piston holder to the free end of said spindle; and a coupling head adapted to selectively couple said conversion piston holder to a piston of a high-pressure syringe or to contact and apply injection pressure to a piston of a manual syringe.

2. A conversion kit according to claim 1, wherein the maximum diameter of said peripheral edge of said manual syringe is equal to or less than the diameter of said guide.

3. A conversion kit according to claim 1, wherein said peripheral edge of said manual syringe includes wing extensions having a maximum diameter of greater than the diameter of said guide, and wherein said first recess in said head includes a first region for receiving said peripheral edge said high-pressure syringe, and a second region for receiving end regions of said wing extensions of said manual syringe.

4. A conversion kit according to claim 1, further including a resilient projection extending around the inner periphery of said guide, and wherein said reducing sleeve includes a recess for receiving said resilient projection when said reducing member is inserted within said guide.

5. A conversion kit according to claim 4, wherein said resilient projection is an O-ring inserted into a groove formed on the inner periphery of said guide.

6. A conversion kit according to claim 1, wherein said peripheral edge of said reducing sleeve is adapted to be substantially non-rotatably received in said first recess in said receiving head.

7. A conversion kit according to claim 3, wherein said peripheral edge of said reducing sleeve includes peripheral edge recesses for receiving said wing extensions of said manual syringe.

8. A conversion kit according to claim 1, wherein said second recess in said reducing sleeve is adapted to substantially non-rotatably receive said peripheral edge of said manual syringe.

9. A conversion kit according to claim 1, wherein said manual syringe has a volume in the range of 30 ml to 50 ml, and wherein said high-pressure syringe has a volume in the range of 50 ml to 200 ml.

10. A conversion kit according to claim 1, wherein said manual syringe has a volume in the range of 1 ml to 50 ml, and wherein said high-pressure syringe has a volume in the range of 50 ml to 200 ml.

11. A conversion kit according claim 1, including more than on conversion vessel, more than one reducing sleeve and more than one conversion piston holder, and adapted to be used with a wide variety of manual syringes having different volumes.

* * * * *